(12) United States Patent
Cunningham et al.

(10) Patent No.: US 10,293,022 B2
(45) Date of Patent: May 21, 2019

(54) PEPTIDE INHIBITORS OF SEROTONIN 5-HT$_{2C}$ RECEPTOR:PTEN INTERACTION

(71) Applicants: Kathryn Cunningham, Galveston, TX (US); Scott Gilbertson, Houston, TX (US)

(72) Inventors: Kathryn Cunningham, Galveston, TX (US); Scott Gilbertson, Houston, TX (US)

(73) Assignees: THE BOARD OF REGENTS OF THE UNIVERSITY OF TEXAS SYTEM, Austin, TX (US); THE UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/450,738

(22) Filed: Mar. 6, 2017

(65) Prior Publication Data
US 2017/0209526 A1 Jul. 27, 2017

Related U.S. Application Data

(62) Division of application No. 14/113,763, filed as application No. PCT/US2012/035672 on Apr. 27, 2012, now Pat. No. 9,611,292.

(60) Provisional application No. 61/479,837, filed on Apr. 27, 2011.

(51) Int. Cl.
*A61K 38/00* (2006.01)
*A61K 39/00* (2006.01)
*A61K 39/40* (2006.01)
*A01N 37/18* (2006.01)
*A61K 38/08* (2019.01)
*C07K 7/06* (2006.01)

(52) U.S. Cl.
CPC ............... *A61K 38/08* (2013.01); *C07K 7/06* (2013.01); *A61K 38/00* (2013.01)

(58) Field of Classification Search
None
See application file for complete search history.

(56) References Cited

PUBLICATIONS

Anastasio, et al., "Peptide inhibitors disrupt the serotonin 5-HT2C receptor interaction with phosphatase and tensin homolog to allosterically modulate cellular signaling and behavior." J Neurosci. 32(4):1615-30, 2013.
Burnet, et al., "Allelic variation of the 5-HT2C receptor in bulimia nervosa and binge eating disorder" Psychiat. Genet. 9(2):101-4, 1999.
Ji, et al., "Disruption of PTEN coupling with 5-HT2X receptors suppresses behavioral responses induced by drugs of abuse." Nat Med. 12(3):324-9, 2006.
Maillet, et al., "PTEN-5-HT2X coupling: a new target for treating drug addiction." Prog Brain Res. 172:407-20, 2008.
International Search Report and Written Opinion in International Application No. PCT/US2012/035672 dated Sep. 26, 2012.

*Primary Examiner* — Olga N Chernyshev
(74) *Attorney, Agent, or Firm* — Norton Rose Fulbright US LLP

(57) ABSTRACT

The inventors have identified how the assembly of the 5-HT2cR with another protein (phosphatase and tensin homologue; PTEN) controls cellular function, and have synthesized a new peptide that interrupts the 5-HT2cR: PTEN complex to result in enhanced 5-HT2cR function.

2 Claims, 13 Drawing Sheets

Specification includes a Sequence Listing.

3L4F  Ac-P-N-Q-D-Q-N-A-R-R-R-K-K-K-E-R-R-NH₂

210  Ac-P-N-Q-D-Q-N-A-R-NH₂

212  Ac-Q-N-A-R-R-R-K-K-NH₂

214  Ac-R-R-K-K-K-E-R-R-NH₂

Fragments of 3L4F were synthesized and tested for activity.

| | | |
|---|---|---|
| 210-A1 | Ac-A-N-Q-D-Q-N-A-R-NH₂ | (-) |
| 210-A2 | Ac-P-A-Q-D-Q-N-A-R-NH₂ | (-) |
| 210-A3 | Ac-P-N-A-D-Q-N-A-R-NH₂ | (-) |
| 210-A4 | Ac-P-N-Q-A-Q-N-A-R-NH₂ | (+) |
| 210-A5 | Ac-P-N-Q-D-A-N-A-R-NH₂ | (-) |
| 210-A6 | Ac-P-N-Q-D-Q-A-A-R-NH₂ | (+) |
| 210-A8 | Ac-P-N-Q-D-Q-N-A-A-NH₂ | (-) |

PEPTIDE INHIBITORS OF SEROTONIN 5-HT$_{2C}$ RECEPTOR:PTEN INTERACTION

This application is a divisional from U.S. application Ser. No. 14/113,763 filed Apr. 28, 2014, which is a 371 national stage of International Application No. PCT/US2012/035672 filed Apr. 27, 2012, which claims priority to U.S. Provisional Patent Application 61/479,837 filed Apr. 27, 2011, each of which is incorporated herein by reference in its entirety.

STATEMENT REGARDING FEDERALLY FUNDED RESEARCH

This invention was made with government support under RO1 DA030977 awarded by the National Institutes of Health. The U.S. government has certain rights in the invention.

BACKGROUND

Embodiments of this invention are directed generally to biology and medicine. Certain embodiments are directed to modulation of serotonin receptors and serotonin receptor complexes.

Serotonin or 5-hydroxytryptamine (5-HT) is a monoamine neurotransmitter. Biochemically derived from tryptophan, serotonin is primarily found in the gastrointestinal (GI) tract, platelets, and in the central nervous system (CNS) of animals including humans.

The serotonin receptors, also known as 5-hydroxytryptamine receptors or 5-HT receptors, are a group of G protein-coupled receptors (GPCRs) and ligand-gated ion channels (LGICs) found in the central and peripheral nervous systems. They mediate both excitatory and inhibitory neurotransmission. There are 6 types or families of G protein coupled 5-HT receptors, 5-HT$_1$, 5-HT$_2$, 5-HT$_4$, 5-HT$_5$, 5-HT$_6$, and 5-HT$_7$. Within each family there can be several subtypes of receptors.

The serotonin receptors modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P, among others. The serotonin receptors influence various biological and neurological processes such as aggression, anxiety, appetite, cognition, learning, memory, mood, nausea, sleep, and thermoregulation. The serotonin receptors are the target of a variety of pharmaceutical and illicit drugs, including many antidepressants, antipsychotics, anorectics, antiemetics, gastroprokinetic agents, antimigraine agents, hallucinogens, and entactogens.

There is a need for additional therapeutic agents that modulate 5-HT receptors, particularly agents that are selective for particular 5-HT receptor types and subtypes.

SUMMARY

The 5-HT$_{2C}$ receptor is implicated in feeding, obesity, palatable food reward, metabolic disorders, drug addiction, anxiety, stress sensitivity, and depression. Embodiments of the invention are directed to modulation of the 5-HT$_{2C}$R. Certain aspects are directed to therapies for the above referenced conditions. In certain aspects, therapeutic agents are identified that disrupt the 5-HT$_{2C}$R:PTEN complex activating 5-HT$_{2C}$R signaling. In certain aspects the complex is disrupted by a disrupter. The disrupter can be a peptide that displaces PTEN from the 5-HT$_{2C}$R:PTEN complex or inhibits the formation of the complex.

In certain embodiments the disrupter is a peptide or peptide mimic, such as a peptoid or other non-natural molecule. In certain aspects, the disrupter is a positive allosteric 5-HT$_{2C}$R modulator. One example of such a disrupter is the 3L4F-210 peptide (PNQDQNAR, SEQ ID NO:2) or mimics or functional variants thereof.

In certain aspects the disrupter is a functional variant of SEQ ID NO:2, including X$_1$NQDQNAR (SEQ ID NO:3), PX$_2$QDQNAR (SEQ ID NO:4), PNX$_3$DQNAR (SEQ ID NO:5), PNQX$_4$QNAR (SEQ ID NO:6), PNQDX$_5$NAR (SEQ ID NO:7), PNQDQX$_6$AR (SEQ ID NO:8), or PNQDQNX$_7$R (SEQ ID NO:9). X$_1$, X$_2$, X$_3$, X$_4$, X$_5$, X$_6$, or X$_7$ can be individually altered to alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y), or valine (val—V) and X$_2$ is selected from alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y), or valine (val—V). In certain aspects, any two residue combinations of residues 1 to 7 of SEQ ID NO:2 can be alter. In a further aspect, any three residue combinations of residues 1 to 7 of SEQ ID NO:2 can be altered. In still a further aspect, any four residue combinations of residues 1 to 7 of SEQ ID NO:2 can be altered. In certain aspects, any five residue combinations of residues 1 to 7 of SEQ ID NO:2 can be altered. A functional variant is a peptide having 1, 2, 3, 4, or 5 amino acid substitutions relative to the amino acid sequence of SEQ ID NO:2 that maintains the ability to disrupt or inhibit the association of 5-HT$_{2C}$R with PTEN in a cell based assay as described herein.

In certain aspects, the 5-HT$_{2C}$R disrupter is a peptide mimic of SEQ ID NO:2, SEQ ID NO:3, SEQ ID NO:4, SEQ ID NO:5, SEQ ID NO:6, SEQ ID NO:7, SEQ ID NO:8, or SEQ ID NO:9.

In certain aspects, a peptide can be a peptide derivative of SEQ ID NO:2, SEQ ID NO:3, SEQ ID NO:4, SEQ ID NO:5, SEQ ID NO:6, SEQ ID NO:7, SEQ ID NO:8, or SEQ ID NO:9. As used herein, a "derivative" of a peptide refers to a form of the peptide in which one or more reactive groups on the peptide have been derivatized with a substituent group. Examples of peptide derivatives include peptides in which an amino acid side chain, a peptide backbone, or an amino- or carboxy-terminus has been modified (e.g., methylation, N-acylation, etc.). The peptide can be modified on one or more of its internal side chains, C terminus, and/or N terminus.

Embodiments include methods of treating addictive or eating disorders comprising administering to a human in need thereof a therapeutically effective amount of a compound that dissociates 5-HT$_{2C}$R and PTEN, or inhibits the association of 5-HT$_{2C}$R and PTEN. In certain aspects the eating disorder is anorexia nervosa, bulimia nervosa, weight-gain after smoking cessation, snacking, or binge eating. In a further embodiment the compound is a peptide mimic of the 3L4F-210 peptide (SEQ ID NO:2), or a functionally active fragment thereof.

The therapies and therapeutic molecules cause a serotonin receptor to remain constitutively active. As contrasted with the more traditional approach of inhibiting reuptake of signal molecules. Thus, presenting a novel mechanism, treatment, and therapeutic approach to binge eating disorders.

The terms "inhibiting," "reducing," or "preventing," or any variation of these terms, when used in the claims and/or the specification includes any measurable decrease or complete inhibition to achieve a desired result.

The term "isolated" can refer to a peptide that is substantially free of cellular material, bacterial material, viral material, column or gel support, culture medium (when produced by recombinant DNA techniques) of their source of origin, or chemical precursors or other chemicals (when chemically synthesized).

Moieties of the invention, such as peptides, may be conjugated or linked covalently or noncovalently to other moieties such as adjuvants, proteins, peptides, fluorescence moieties, or labels. The term "conjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise a pharmaceutically acceptable excipient.

The term "providing" is used according to its ordinary meaning to indicate "to supply or furnish for use." In some embodiments, the peptide is provided directly by administering the peptide, while in other embodiments, the peptide is effectively provided by administering a nucleic acid that encodes the peptide. In certain aspects the invention contemplates compositions comprising various combinations of nucleic acids and/or peptides.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

DESCRIPTION

Figure 1:
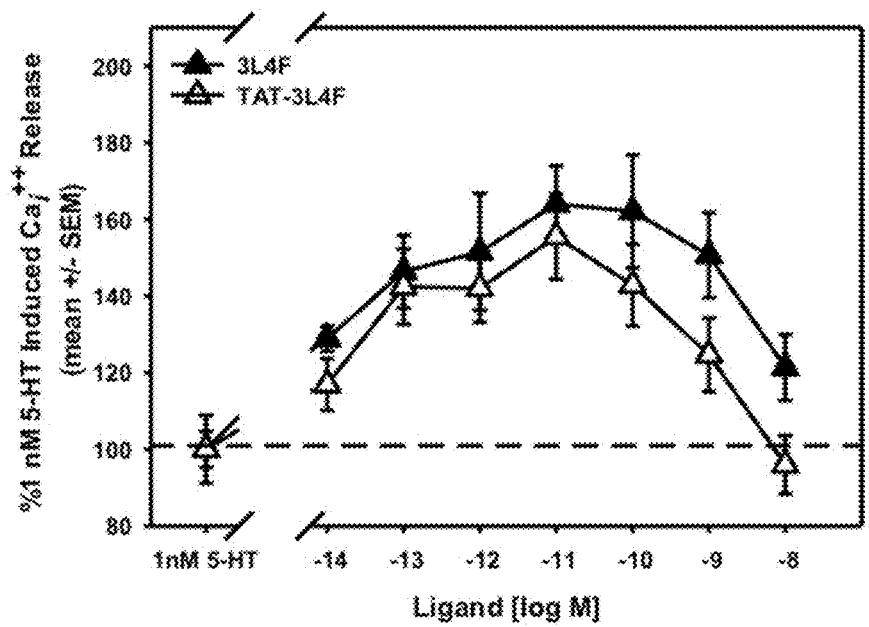
FIG. 1 shows that 3L4F and TAT-3L4F increase 5-HT (1 nM) Induced $Ca_i^{++}$ release in $5\text{-}HT_{2C}R$-CHO cells.

Therapeutic gains in addictive, psychiatric, and neurological disorders may be achieved through the selective and sustained activation of the brain-specific serotonin 5-HT$_{2C}$ receptor (or 5-HT$_{2C}$R). The inventors have identified how the assembly of the 5-HT$_{2C}$R with another protein (phosphatase and tensin homologue; PTEN) controls cellular function, and have synthesized peptides that interrupt the 5-HT$_{2C}$R:PTEN complex to result in enhanced 5-HT$_{2C}$R function. An assay has been established and can be used to screen disrupters of the 5-HT$_{2C}$R:PTEN complex. Studies involve analyses of peptides in animal models for the treatment of addictive, psychiatric, and neurological disorders. Accordingly, the indications that may benefit from these disrupters include: addictive disorders such as addictions to food, drugs, alcohol, and nicotine; psychiatric disorders such as depression and schizophrenia; and neurological disorders such as Parkinson's disease. These studies are the first step to identifying novel therapeutics to disrupt this protein complex.

PTEN (phosphatase and tensin homolog) is a major "break" on growth factor signaling (Li et al., 1997; Endersby and Baker, 2008); it is a tumor suppressor that is lost in many cancers (Keniry and Parsons, 2008). It is involved in brain development (Lachyankar et al. 2000) and is expressed in reward circuits of adult brain that control palatable food intake (Cai et al., 2009). 5-HT$_{2C}$R activity is suppressed by PTEN association. Activity of the 5-HT$_{2C}$R is increased upon dissociation of the 5-HT$_{2C}$R:PTEN complex. Embodiments of the invention are directed to modulation of the 5-HT$_{2C}$R:PTEN complex. In certain aspects the complex is disrupted by a disrupter. The disrupter can be a peptide that displaces PTEN from the 5-HT$_{2C}$R:PTEN complex or inhibits the formation of the complex. In a further embodiment the disrupter is a mimic of a peptide, such as a peptoid or other non-natural molecule. The disrupter can act as a positive allosteric 5-HT$_{2C}$R modulator.

I. Polypeptides and Peptides

The 3L4F peptide (PNQDQNARRRKKKERR (SEQ ID NO:1) was identified as a disrupter of 5-HT$_{2C}$R:PTEN association. Fragment 210 (3L4F-210)(PNQDQNAR (SEQ ID NO:2) was identified as an active fragment of the 3L4F peptide. Alanine scanning mutagenesis indicates that residues 1, 2, 3, 4, 5, 6, or 7 of SEQ ID NO:2, can be altered individually without causing a substantial decrease in activity. Thus, functional variants of SEQ ID NO:2 include $X_1$NQDQNAR (SEQ ID NO:3), P$X_2$QDQNAR (SEQ ID NO:4), PN$X_3$DQNAR (SEQ ID NO:5), PNQ$X_4$QNAR (SEQ ID NO:6), PNQD$X_5$NAR (SEQ ID NO:7), PNQDQ$X_6$AR (SEQ ID NO:8), or PNQDQN$X_7$R (SEQ ID NO:9). $X_1$, $X_2$, $X_3$, $X_4$, $X_5$, $X_6$, or $X_7$ can be individually altered to alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y), or valine (val—V) and $X_2$ is selected from alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y), or valine (val—V). In certain aspects, any two residue combinations of residues 1 to 7 of SEQ ID NO:2 can be alter. In a further aspect, any three residue combinations of residues 1 to 7 of SEQ ID NO:2 can be altered. In still a further aspect, any four residue combinations of residues 1 to 7 of SEQ ID NO:2 can be altered. In certain aspects, any five residue combinations of residues 1 to 7 of SEQ ID NO:2 can be altered. Fragment 212 (QNARRRKK (SEQ ID NO:10) and 214 (RRKKKERR (SEQ ID NO:11) demonstrated less disrupting activity than the 210 fragment.

In some embodiments, $X_1$, $X_2$, $X_3$, $X_4$, $X_5$, $X_6$, or $X_7$ are independently selected from any amino acid. $X_1$, $X_2$, $X_3$, $X_4$, $X_5$, $X_6$, or $X_7$ can be independently selected from the group of 20 natural amino acids. In some instances, $X_1$, $X_2$, $X_3$, $X_4$, $X_5$, $X_6$, or $X_7$ are conservative amino acid substitutions relative to the residues of SEQ ID NO:2. Conservative substitutions of amino acids as known to those skilled in the art are within the scope of the present invention, as long as disrupter activity is preserved in the substituted peptide. Conservative amino acid substitutions include replacement of one amino acid with another having the same type of functional group or side chain, e.g. aliphatic, aromatic, positively charged, negatively charged. These substitutions may enhance oral bioavailability, penetration into the central nervous system, targeting to specific cell populations and the like. Conservative substitution tables providing functionally similar amino acids are well known in the art. Families of amino acid residues having similar side chains have been defined. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a peptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine). Thus, in some embodiments, $X_1$ is A, V, L, I, F, M, or W. In some embodiments, $X_2$ is G, Q, S, T, Y, or C. In some embodiments, $X_3$ is G, N, S, T, Y, or C. In some embodiments, $X_4$ is E. In some embodiments, $X_5$ is G, N, S, T, Y, or C. In some embodiments, $X_6$ is G, Q, S, T, Y, or C. In some embodiments, X7 is S, V, L, I, P, F, M, or W.

The peptides of the present invention may be synthesized chemically using methods known in the art for synthesis of peptides and polypeptides. These methods generally rely on the known principles of peptide synthesis; most conveniently, the procedures can be performed according to the known principles of solid phase peptide synthesis.

As used herein "peptide" indicates a sequence of amino acids linked by peptide bonds. A polypeptide is generally a peptide of about 51 and more amino acids.

Peptide analogs and peptidomimetics are also included within the scope of the invention as well as salts and esters of the polypeptides of the invention are encompassed.

A peptide analog according to the present invention may optionally comprise at least one non-natural amino acid and/or at least one blocking group at either the C terminus or N terminus.

The term "peptidomimetic" or "peptide mimic" means that a peptide according to the invention is modified in such a way that it includes at least one non-peptidic bond such as, for example, urea bond, carbamate bond, sulfonamide bond, hydrazine bond, or any other covalent bond.

In certain aspects, peptides of the invention are modified. Main sequence modifications include unusual amino acids such as D-amino acids, phosphorylated amino acids (Ser, Thr, Tyr), glycosylated amino acids (Ser, Thr, Asn), (β-amino acids, GABA, ω-amino acids.

Carboxy terminal modifications include acylation with carboxylic acids: formic, acetic, propionic, fatty acids (myristic, palmitic, stearic), succinic, benzoic, carbobenzoxy (Cbz); and biotinylation.

Amino terminal modifications include:
(i) acylation with carboxylic acids: formic, acetic, propionic, fatty acids (myristic, palmitic, stearic, etc) succinic, benzoic, carbobenzoxy (Cbz);
(ii) biotinylation;
(iii) attachment of dyes such as fluorescein (FITC, FAM, etc.), 7-hydroxy-4-methylcoumarin-3-acetic acid, 7-hydroxycoumarin-3-acetic acid, 7-metoxycoumarin-3-acetic acid and other coumarins; rhodamines (5-carboxyrhodamine 110 or 6G, 5(6)-TAMRA, ROX, etc); N-[4-(4-dimethylamino)phenylazo]bezoic acid (Dabcyl), 2,4-dinitrobenzene (Dnp), 5-dimethylaminonaphthalene-1-sulfonic acid (Dansyl) and other dyes; and
(iv) polyethyleneglycol.

Side chain modifications can include:
(i) Cysteine (Cys) selectively modified with derivatives of fluorescein (FITC, IAF), rhodamines (5-TMRIA, 5-TRITC G, etc), 5-[(2-aminoethyl)amino]naphtalene-1-sulfonic acid (EDANS) (EDANS C2 maleimide or iodoacetamide); other dyes, PEGs;
(ii) Lysine/Ornitine (Lys/Orn) selectively modified with biotin; acylated with carboxylic acids: acetic, propionic, fatty acids (myristic, palmitic, stearic, etc) succinic, benzoic, etc; dyes such as fluorescein (FITC, FAM, etc), 7-hydroxy-4-methylcoumarin-3 -acetic acid, 7-hydroxycoumarin-3-acetic acid, 7-metoxycoumarin-3-acetic acid and other coumarins; rhodamines (5-carboxyrhodamine 110 or 6G, 5(6)-TAMRA, ROX, etc) N-[4-(4-dimethylamino)phenylazo]bezoic acid (Dabcyl), 2,4-dinitrobenzene (Dnp), 5-dimethylaminonaphthalene-1-sulfonic acid (Dansyl) and other dyes; or PEGs;
(iii) Aspartic/Glutamic acids (Asp/Glu) modified with N-alkyl amides (alkyl=methyl, ethyl, propyl, octyl, benzyl, etc.), polyethylene glycols (PEGs), amides with α,ω-alkyl-diamines (ethylenediamine, 1,3-diamino propane, putrescine, cadaverine, diamino PEGs, etc), piperazine, spermine, spermidine, etc; Biotin (connected through a linker); dyes such as 5-[(2-aminoethyl)amino]naphthalene-1-sulfonic acid (EDANS), fluorescein (AMF, FITC cadaverine, FAM with linkers, etc), 7-amino-4-trifluoromethyl coumarin (AFC), 7-amino-4-methyl coumarin (AMC), other coumarins; rhodamines (TAMRA, ROX, sulforhodamine 101, etc) and other dyes; Esters: methyl, ethyl, benzyl, etc.

Salts and esters of the peptides of the invention are encompassed within the scope of the invention. Salts of the peptides of the invention are physiologically acceptable organic and inorganic salts. Functional derivatives of the peptides of the invention may be prepared from the functional groups that occur as side chains on the residues or the N- or C-terminal groups, by means known in the art, and are included in the invention as long as they do not destroy the activity of the peptide and do not confer toxic properties on compositions containing it. These derivatives include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "amino acid" refers to compounds that have an amino group and a carboxylic acid group, preferably in a 1,2-; 1,3-; or 1,4-substitution pattern on a carbon backbone. β-Amino acids are most preferred, and include the 20 natural amino acids (which are L-amino acids except for glycine and which are found in proteins), the corresponding D-amino acids, the corresponding N-methyl amino acids, side chain modified amino acids, biosynthetically available amino acids (which are not found in proteins, e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art.

The amino acids used in this invention are available commercially or are available by routine synthetic methods. Certain residues may require special methods for incorporation into the peptide, and sequential, divergent or convergent synthetic approaches to the peptide sequence are useful in this invention. Natural coded amino acids and their derivatives are represented by three-letter codes according to IUPAC conventions. When there is no indication, the L isomer was used.

Variants of the peptides have at least or about 37, 50, 62, 75, or 87% or more identity to SEQ ID NO:1 or SEQ ID NO:2. According to some embodiments, 1, 2, 3, 4, or 5 residues may be altered with the resulting peptide maintaining its disrupter function. Percentage identity refers to the number of identical amino acids between the two compared peptide sequences over a particular length.

II. Pharmaceutical Formulations

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non-limiting example, oral, rectal, transdermal, subcutaneous, intravenous, intramuscular and intranasal. Depending upon the intended route of delivery, the compounds of this invention are preferably formulated as either injectable or oral compositions.

The compounds described herein can be administered at a dose of 0.001, 0.01, 0.1, 1, 10, 100 μg, ng, or mg per dose. In certain aspects, the compounds in the composition will be administered orally, rectally, transdermally, nasally or by injection, in the form of pharmaceutical formulations comprising the active ingredients in a pharmaceutically acceptable dosage form. The dosage form may be a solid, semisolid or liquid formulation. Usually the active substances will constitute between 0.1, 1, 10, 20, 30, 40, 50, 60, 70, 80, 90, to 99%, including all values and ranges there between, by weight of the formulation, more specifically between 0.5 and 20% by weight for formulations intended for injection and between 0.2 and 50% by weight for formulations suitable for oral administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like. Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

The compounds and compositions of the invention can also be administered in sustained release forms or from sustained release drug delivery systems. A description of representative sustained release materials can be found in Remington's Pharmaceutical Sciences.

To produce pharmaceutical formulations of the composition of the invention in the form of dosage units for oral application, the selected compounds may be mixed with a solid excipient, e.g., lactose, saccharose, sorbitol or mannitol; starches such as potato starch, corn starch or amylopectin; cellulose derivatives; a binder such as gelatin or polyvinylpyrrolidone; disintegrants, e.g., sodium starch glycolate, cross-linked PVP and crosscaramellose sodium; a lubricant such as magnesium stearate, calcium stearate, polyethylene glycol, waxes, paraffin, and the like; and an antisticking agent such as talc or colloidal silicon dioxide, and then compressed into tablets. If coated tablets are required, the cores, prepared as described above, may be coated with a polymer known to one of skill in the art, e.g., HPMC, HC or other cellulose derivatives, or PVP, wherein the polymer is dissolved in water or a readily volatile organic solvent or mixture of organic solvents. Alternatively, the tablets can be coated with a concentrated sugar solution which may contain, e.g., gum arabic, gelatin, talcum, titanium dioxide, and the like. Dyestuffs may be added to these coatings in order, for instance, to readily distinguish between tablets containing different active substances or different amounts of the active compounds.

For the formulation of soft gelatin capsules, the active substances may be admixed with, e.g., a vegetable oil or polyethylene glycol. Hard gelatin capsules may contain granules of the active substances using any of the above mentioned excipients for tablets, e.g., lactose, saccharose, sorbitol, mannitol, starches (e.g. potato starch, corn starch or amylopectin), cellulose derivatives, plasticizers, polytheneglycol, waxes, lipids or gelatin. Also, liquids or semisolids of the drug can be filled into hard gelatin capsules.

Dosage units for rectal application can be solutions or suspensions or can be prepared in the form of suppositories comprising the active substances in a mixture with a neutral fatty base, or gelatin rectal capsules comprising the active substances in admixture with vegetable oil or paraffin oil. Liquid formulations for oral application may be in the form of solutions, syrups or suspensions, for example solutions containing from about 0.2% to about 20% by weight of the active substances herein described, the balance being sugar and a mixture of ethanol, water, glycerol and propylene glycol. Optionally such liquid formulations may contain coloring agents, flavoring agents, saccharin and carboxymethyl cellulose as a thickening agent or other excipients known to a person skilled in the art.

Solutions for parenteral applications by injection can be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

Suitable daily doses of the active compounds in the composition of the invention in therapeutic treatment of humans are about 0.01-100 mg/kg bodyweight for peroral administration and 0.001-100 mg/kg bodyweight for parenteral administration.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice.

However, those of skill in the art should, in light of the present disclosure, appreciate that many changes can be made in the specific embodiments which are disclosed and still obtain a like or similar result without departing from the spirit and scope of the invention.

Example 1

Structural Analyses of $5\text{-HT}_{2C}\text{R:PTEN}$ Complex

The $5\text{-HT}_{2C}\text{R:PTEN}$ complex occurs in rat brain regions implicated in palatable food reward. The $5\text{-HT}_{2C}\text{R:PTEN}$ complex can be demonstrated in $\text{h}5\text{-HT}_{2C}\text{RCHO}$ cells that have a native PTEN. These cells have been employed for $5\text{-HT}_{2C}\text{R}$ signaling studies. Immunohistochemistry demonstrates that $5\text{-HT}_{2C}\text{R}$ and PTEN are in direct contact in cells. Providing 3L4F and fragments thereof disrupt the complex in the cell and result in the lack of co-localization of the molecules by immunohistochemistry or by immunoprecipitation studies. $5\text{-HT}_{2C}\text{R}$ and PTEN can be co-immunoprecipitated from brain tissue samples. Additional studies using the split luciferase assay also detect direct coupling of $5\text{-HT}_{2C}\text{R}$ with PTEN.

Figure 5:
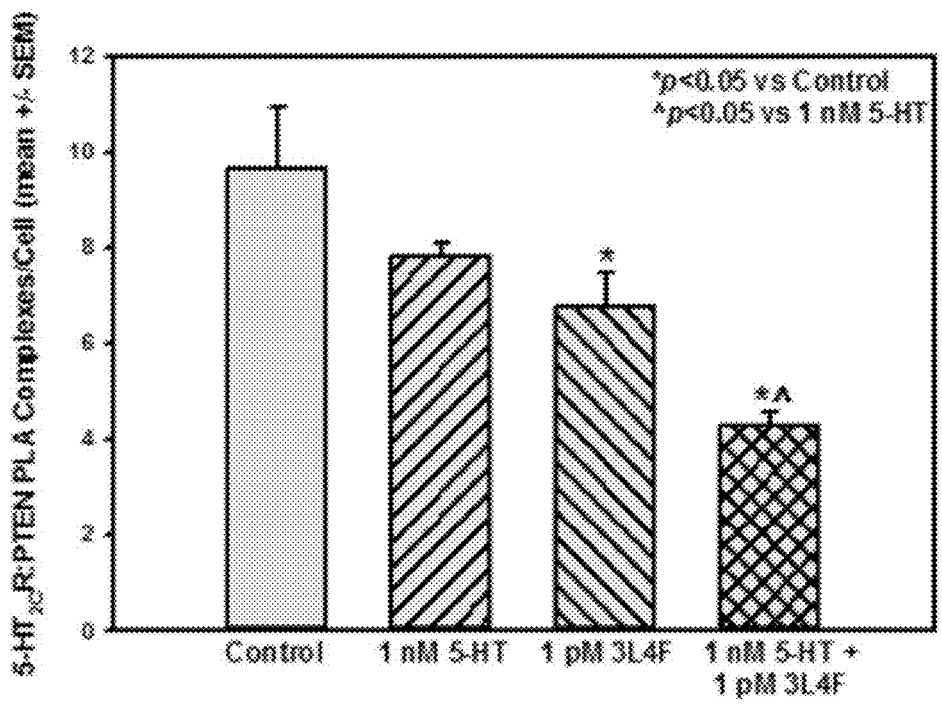
FIG. 5 shows that 3L4F disrupts association of $5\text{-}HT_{2C}R$ and PTEN.

Peptides described herein enhance $5\text{-HT}_{2C}\text{R}$ signaling and peptide disruption of the serotonin (5-HT) $5\text{-HT}_{2C}\text{R}$ interaction with protein phosphatase and tensin (PTEN). This interaction is functionally important to the $5\text{-HT}_{2C}\text{R}$ signalosome. FIG. 5 shows by quantitation of in situ localization studies that direct contact of $5\text{-HT}_{2C}\text{R:PTEN:3L4F}$ disrupts the association.

Figure 6:
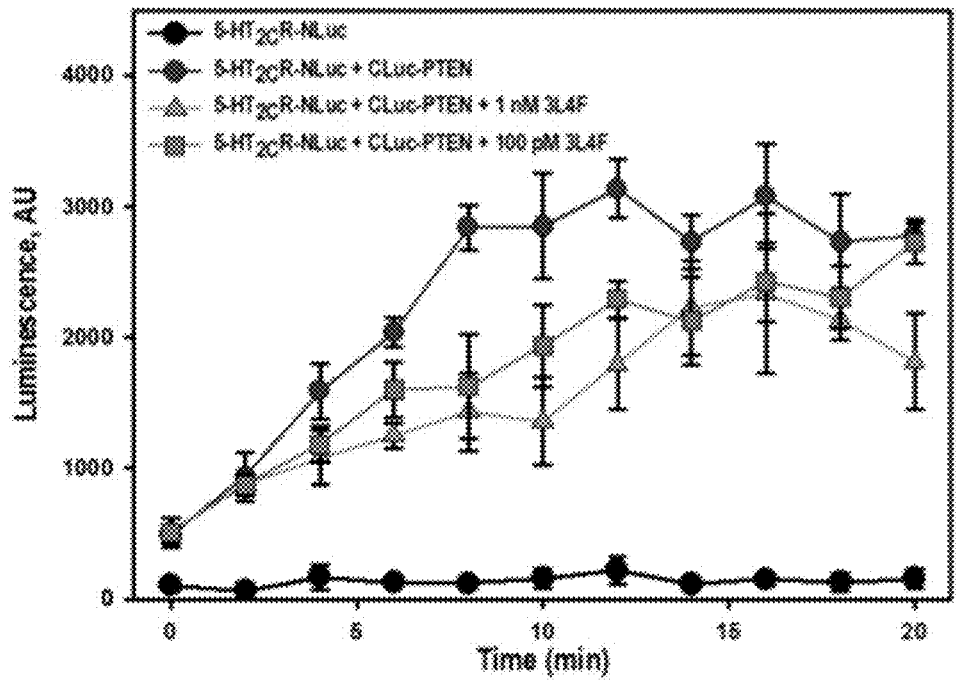
FIG. 6 shows the results of a split luciferase assay indicating 3L4F disruption of direct $5\text{-}HT_{2C}R$:PTEN interaction in live cells using NLuc fused to the third intracellular loop of $5\text{-}HT_{2C}R$ and CLuc fused to PTEN.
Figure 7:
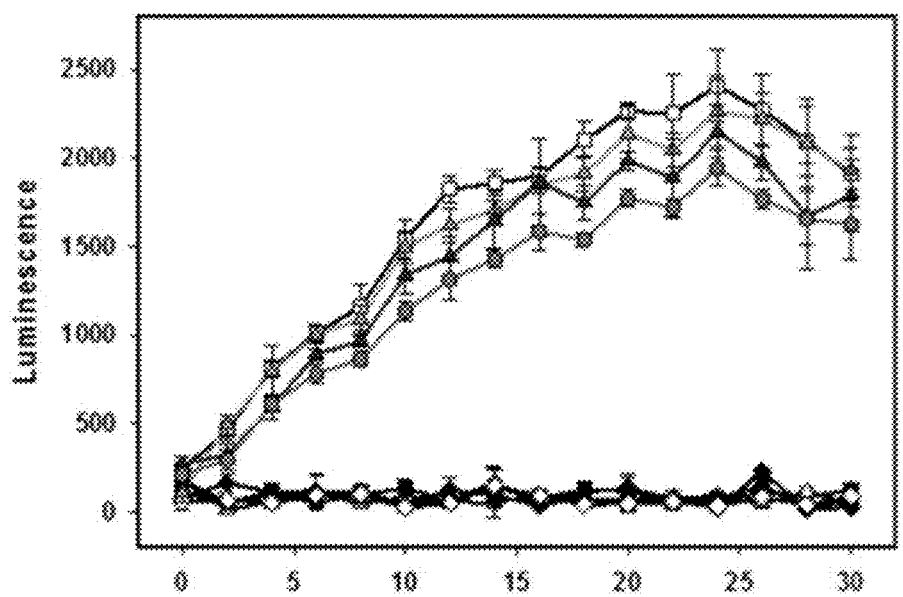
FIG. 7 shows the results of a split luciferase assay showing 3L4F disruption of direct $5\text{-}HT_{2C}R$:PTEN interaction in live cells using NLuc fused to the full length $5\text{-}HT_{2C}R$.

In addition split luciferase assays were used to detect direct coupling of $5\text{-HT}_{2C}\text{R}$ with PTEN. FIG. 6 shows that 3L4F disrupts direct 5-HT2CR:PTEN interaction in live cells using the 3rd intracellular loop of 5-HT2CR is fused to NLuc. FIG. 7 shows that 3L4F disrupts direct $5\text{-HT}_{2C}\text{R:}$ PTEN interaction in live cells using the full length $5\text{-HT}_{2C}\text{R}$ fused to NLuc Example 2

Functional Analysis of $5\text{-HT}_{2C}\text{R:PTEN}$ Complex

Figure 2:
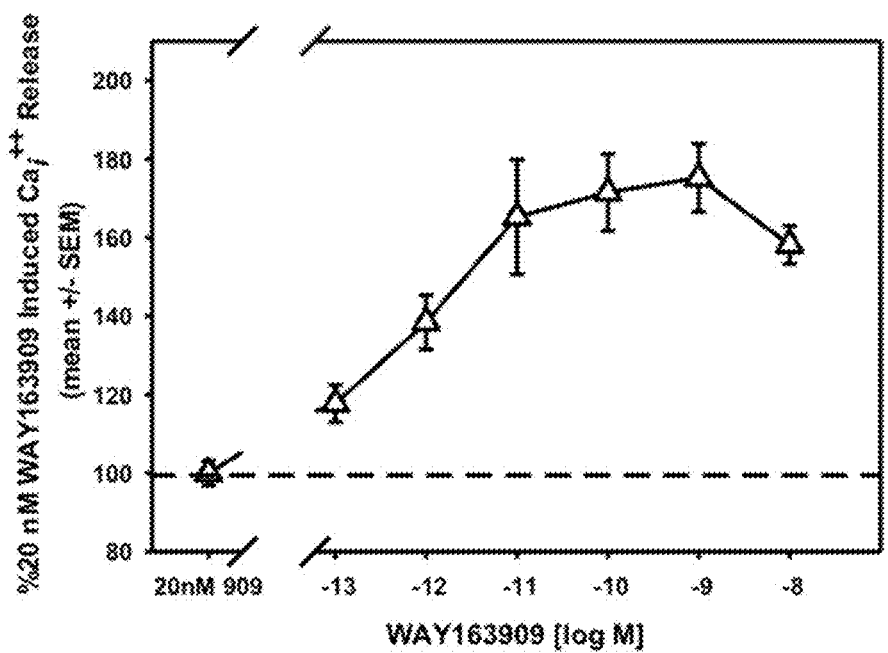
FIG. 2 shows that 3L4F potentiates $Ca_i^{++}$ release induced by the selective orthosteric $5\text{-}HT_{2C}R$ agonist WAY163909 in $5\text{-}HT_{2C}R$-CHO cells.
Figure 3:
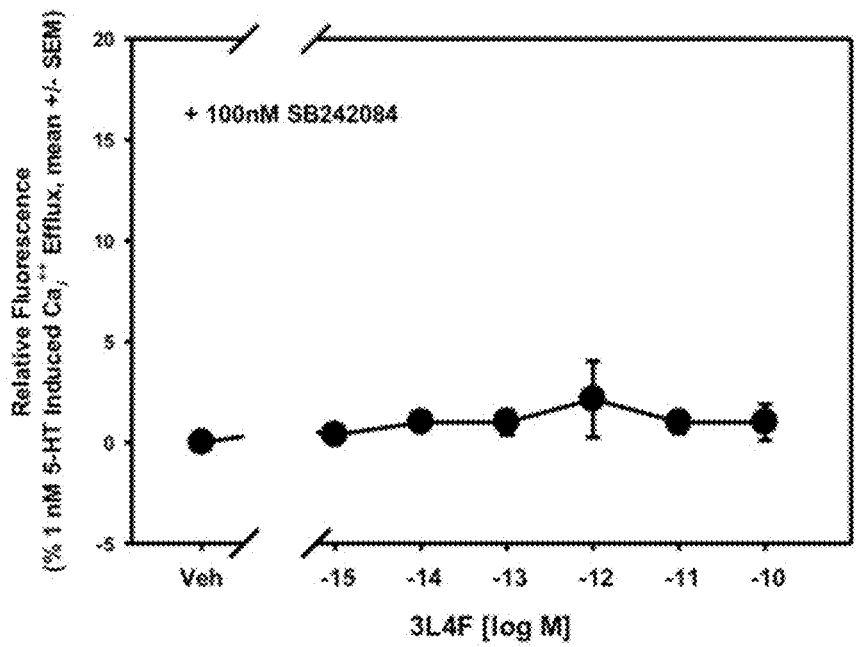
FIG. 3 shows that $5\text{-}HT_{2C}R$ antagonist inhibits 3L4F-enhanced 5-HT induced $Ca_i^{++}$ release in $5\text{-}HT_{2C}R$-CHO cells.
Figure 4:
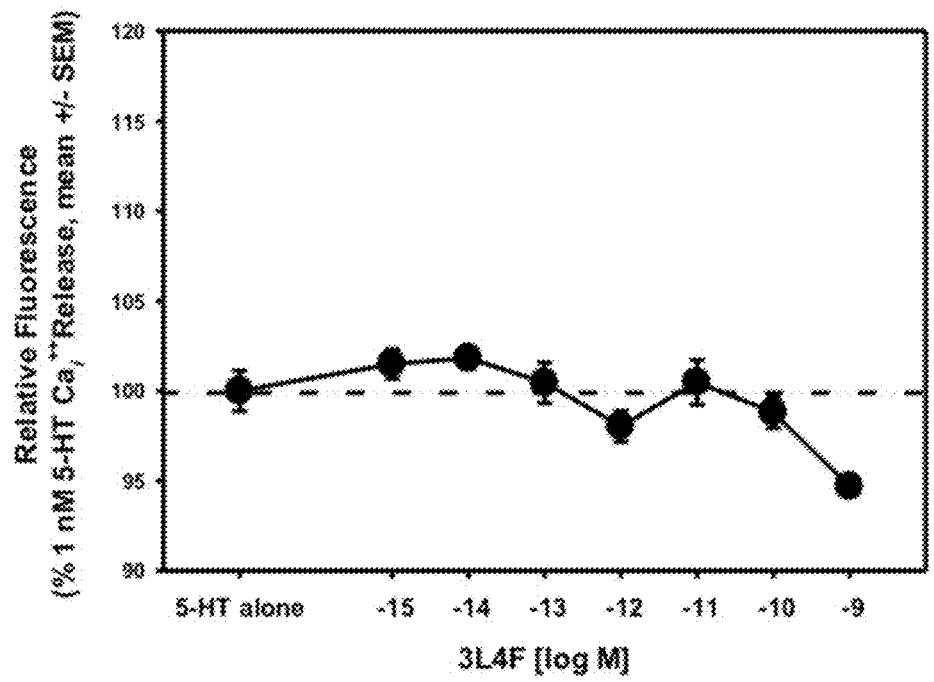
FIG. 4 shows that 3L4F does not alter 5-HT induced $Ca_i^{++}$ release in $5\text{-}HT_{2A}R$-CHO cells.

Functional analysis of the complex was investigated using $\text{Ca}_i^{++}$ release in $5\text{-HT}_{2C}\text{R-CHO}$ cells. Providing 3L4F or an active fragment thereof enhances 5-HT-evoked $\text{Ca}_i^{++}$ release in $5\text{-HT}_{2C}\text{R-CHO}$ cells. FIG. 1 shows that 3L4F and TAT-3L4F increase 5-HT (1 nM) induced $\text{Ca}_i^{++}$ release in $5\text{-HT}_{2C}\text{R-CHO}$ cells. FIG. 2 shows that 3L4F but not the $5\text{-HT}_{2C}\text{R}$ N-terminus peptide fragment V27-R45 alters 5-HT (1 nM) induced $\text{Ca}_i^{++}$ release in $5\text{-HT}_{2C}\text{R-CHO}$ cells. FIG. 3 shows that 3L4F potentiates WAY163909 induced $\text{Ca}_i^{++}$ release in $5\text{-HT}_{2C}\text{R-CHO}$ cells. FIG. 4 shows that $5\text{-HT}_{2C}\text{R}$ antagonist inhibits 3L4F-Enhanced 5-HT Induced $\text{Ca}_i^{++}$ Release in $5\text{-HT}_{2C}\text{R-CHO}$ cells. FIG. 5 shows that 3L4F does not alter 5-HT induced $\text{Ca}_i^{++}$ release in $5\text{-HT}_{2A}\text{R-}$ CHO cells. The studies have shown that the 3L4F peptide enhances $\text{Ca}_i^{++}$ release via a $5\text{-HT}_{2C}\text{R}$ specific mechanism acting down stream ligand binding.

Example 3

Defining the Active Peptide

Figure 8:
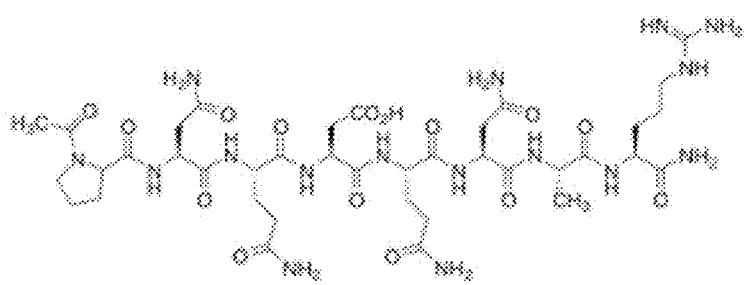
FIG. 8 shows examples of peptide fragments of 3L4F used to define the minimum active peptide.
Figures 9, 10:
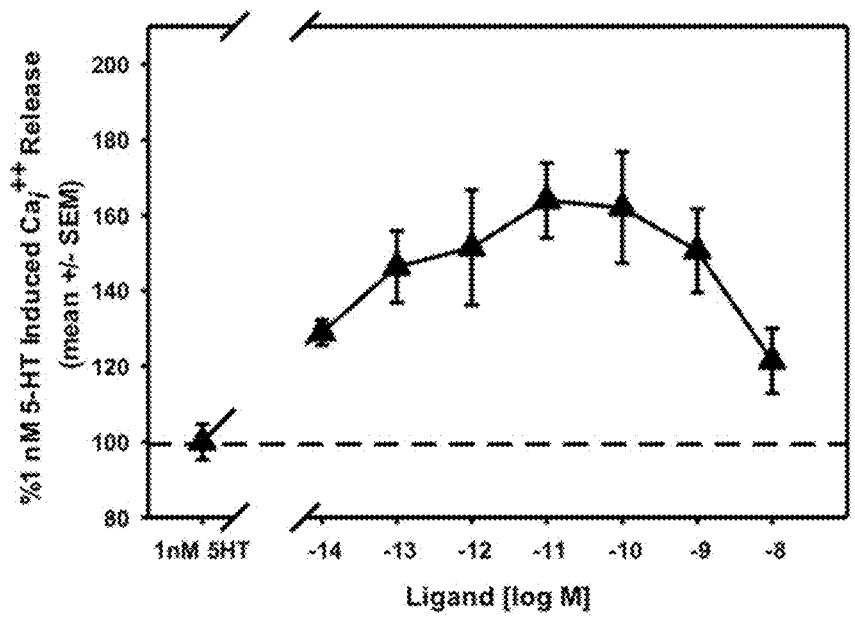
FIG. 9 shows an illustration of the alanine scanning strategy used to further define which residues contribute to 3L4F activity.
FIG. 10 shows that 3L4F increases 5-HT (1 nM) induced $Ca_i^{++}$ release in $5\text{-}HT_{2C}R$-CHO cells.

Alanine scan mutagenesis was used to determine which residues in the 3L4F peptide could be altered without affecting peptide function. FIG. 8 illustrates an example of peptides derived from 3L4F. Peptide 210 was shown to retain 3L4F activity. FIG. 9 illustrates the alanine scanning strategy to identify those amino acids that participate in the activity of the 210 peptide.

Figure 11:
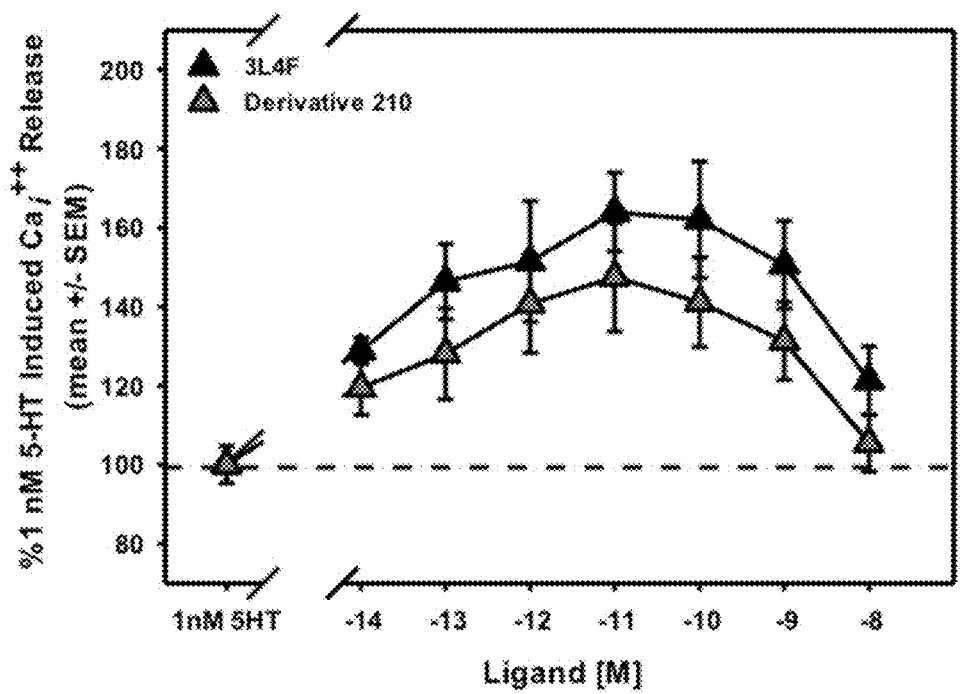
FIG. 11 shows that 3L4F and derivative 210 increase 5-HT (1 nM) induced $Ca_i^{++}$ release in $5\text{-}HT_{2C}R$-CHO cells.
Figure 12:
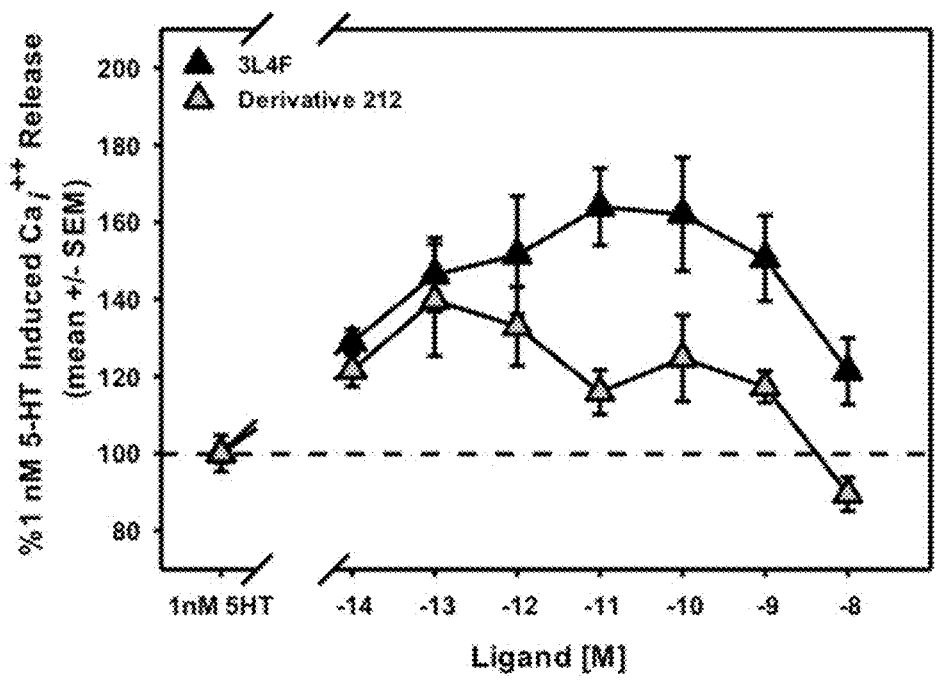
FIG. 12 shows that derivative 212 is less efficacious than 3L4F to increase 5-HT (1 nM) induced $Ca_i^{++}$ release in $5\text{-}HT_{2C}R$-CHO cells.
Figure 13:
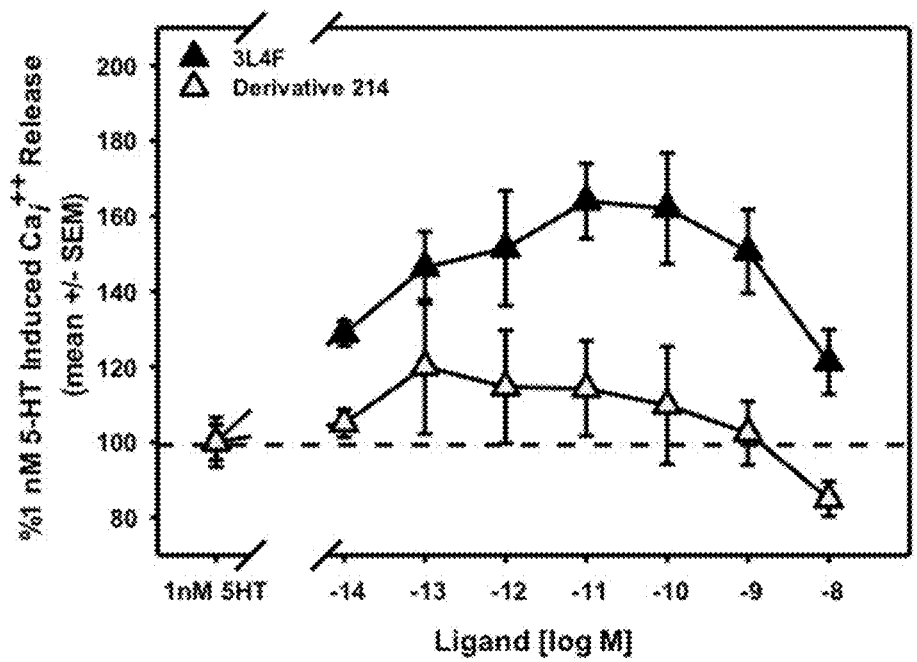
FIG. 13 shows that derivative 214 is less efficacious than 3L4F to increase 5-HT (1 nM) induced $Ca_i^{++}$ release in $5\text{-}HT_{2C}R$-CHO cells.
Figure 14:
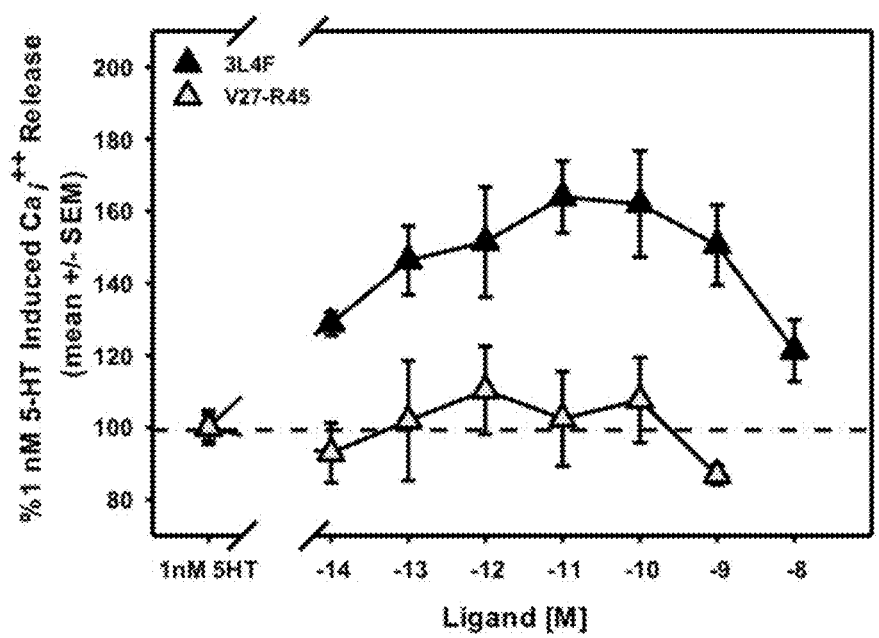
FIG. 14 shows that V27-R45 N-terminus peptide is inactive against 5-HT induced $Ca_i^{++}$ release in $5\text{-}HT_{2C}R$-CHO cells.

FIG. 10 shows that 3L4F increases 5-HT (1 nM) induced $\text{Ca}_i^{++}$ release in $5\text{-HT}_{2C}\text{R-CHO}$ cells. FIG. 11 shows that 3L4F and derivative 210 increase 5-HT (1 nM) induced $\text{Ca}_i^{++}$ release in $5\text{-HT}_{2C}\text{R-CHO}$ cells. FIG. 12 shows that derivative 212 is less efficacious than 3L4F to increase 5-HT (1 nM) induced $\text{Ca}_i^{++}$ release in $5\text{-HT}_{2C}\text{R-CHO}$ cells. FIG. 13 shows that derivative 214 is less efficacious than 3L4F to increase 5-HT (1 nM) induced $\text{Ca}_i^{++}$ release in $5\text{-HT}_{2C}\text{R-}$ CHO cells. FIG. 14 shows that V27-R45 N-terminus peptide is inactive against 5-HT induced $\text{Ca}_i^{++}$ release in $5\text{-HT}_{2C}\text{R-}$ CHO cells. Evaluations of fragments 210, 212, and 214 indicate that the most active part of the peptide is localized to fragment 210 suggesting that this section of the peptide is responsible for the $5\text{-HT}_{2C}\text{R}$ interaction with PTEN.

Figure 15:
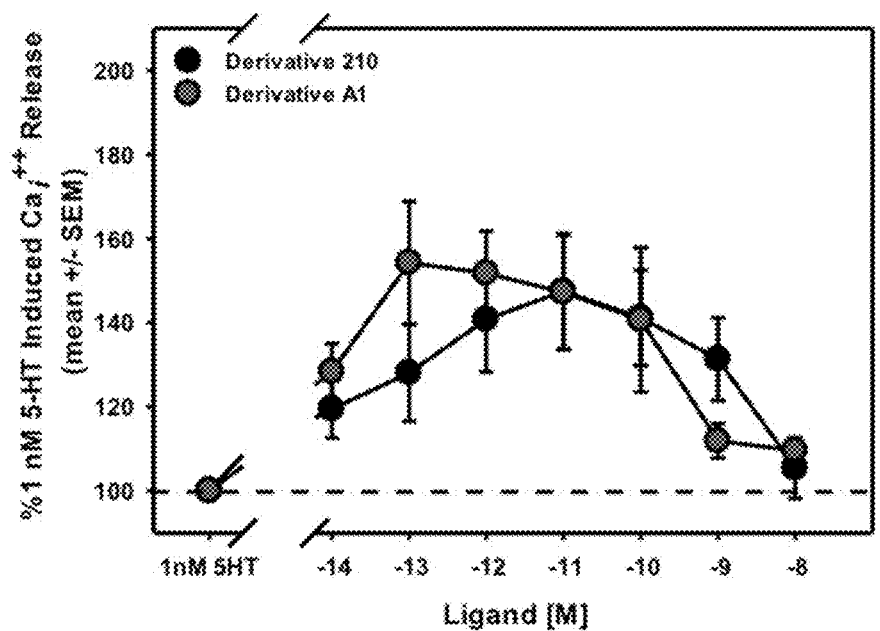
FIG. 15 compares the efficacy of derivatives 210 and A1 in terms of %1 nM 5-HT induced $Ca_i^{++}$ release in $5\text{-}HT_{2C}R$-CHO cells.
Figure 16:
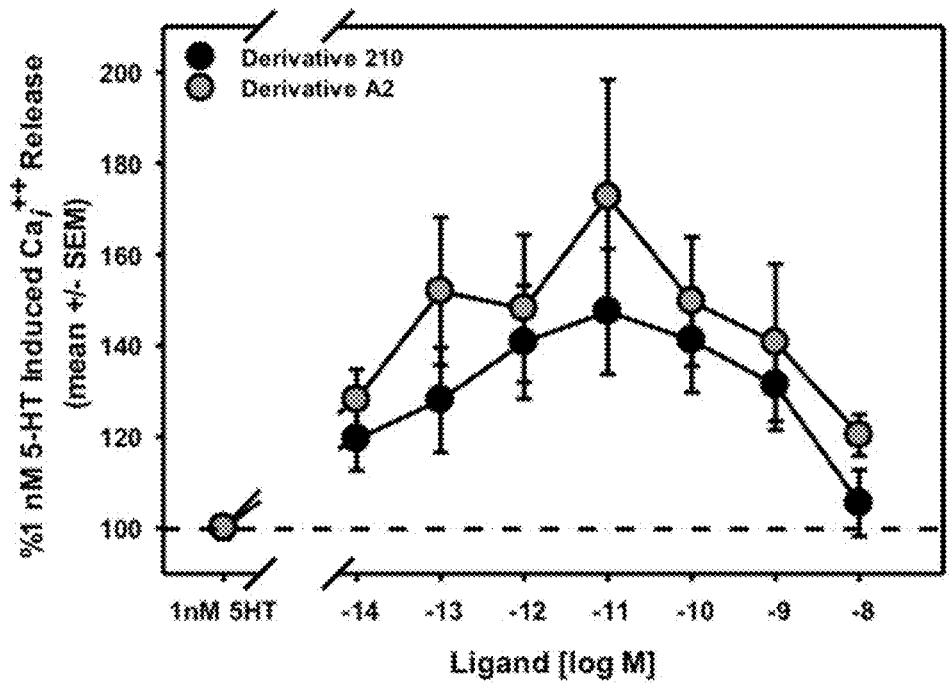
FIG. 16 compares the efficacy of derivatives 210 and A2 in terms of %1 nM 5-HT induced $Ca_i^{++}$ release in $5\text{-}HT_{2C}R$-CHO cells.
Figure 17:
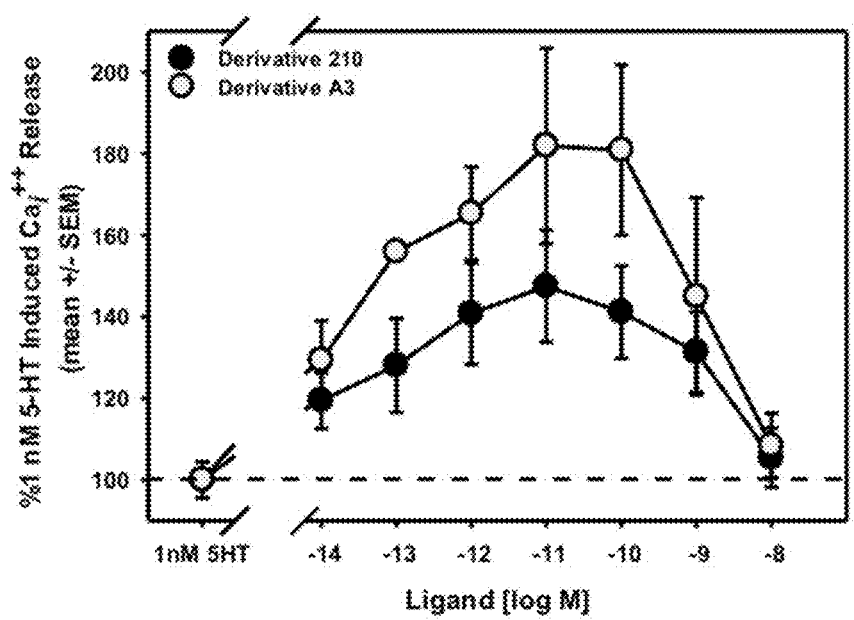
FIG. 17 compares the efficacy of derivatives 210 and A3 in terms of %1 nM 5-HT induced $Ca_i^{++}$ release in $5\text{-}HT_{2C}R$-CHO cells.
Figure 18:
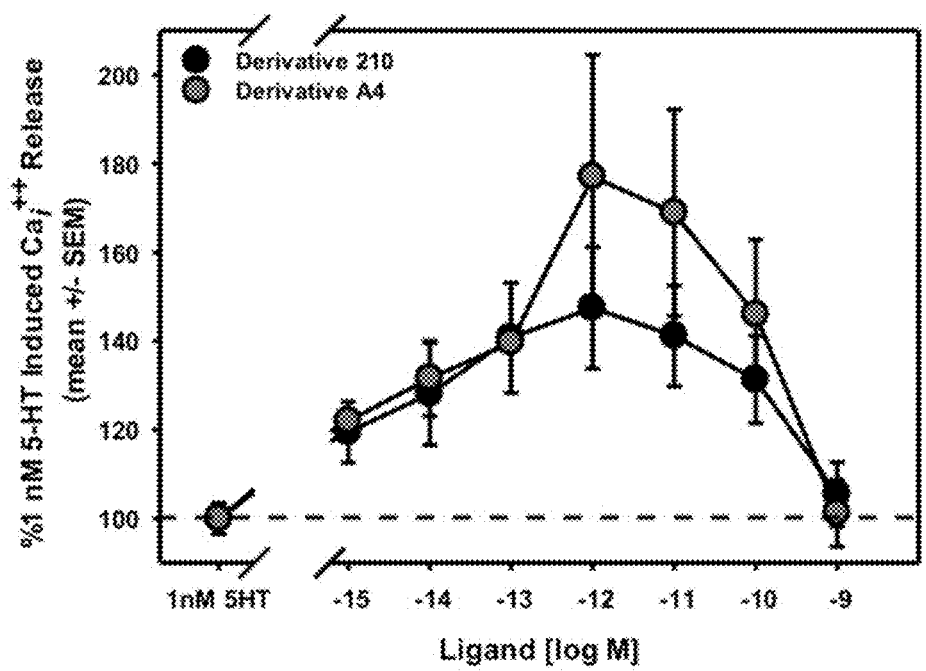
FIG. 18 compares the efficacy of derivatives 210 and A4 in terms of %1 nM 5-HT induced $Ca_i^{++}$ release in 5-HT$_{2C}$R-CHO cells.
Figure 19:
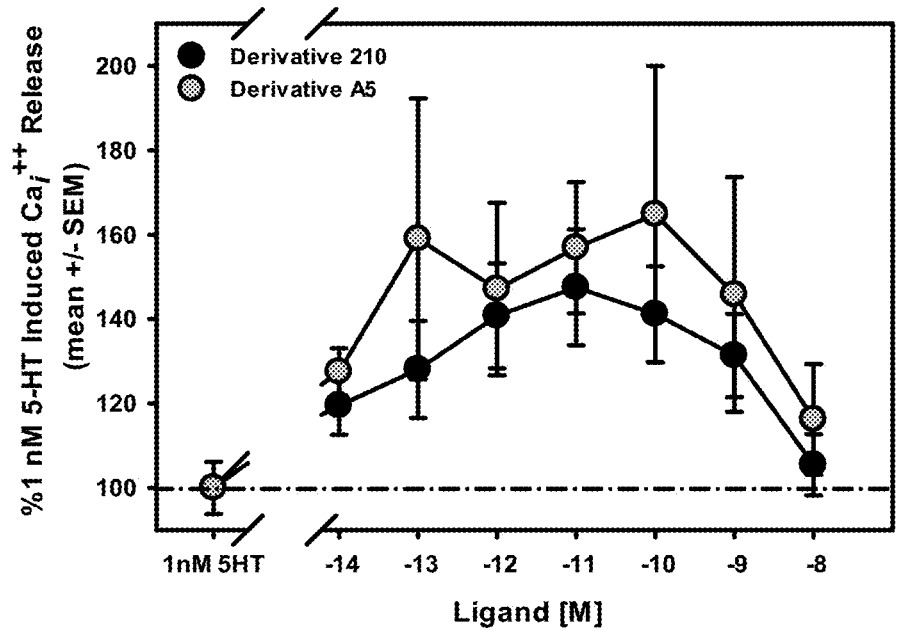
FIG. 19 compares the efficacy of derivatives 210 and A5 in terms of %1 nM 5-HT induced $Ca_i^{++}$ release in 5-HT$_{2C}$R-CHO cells.
Figure 20:
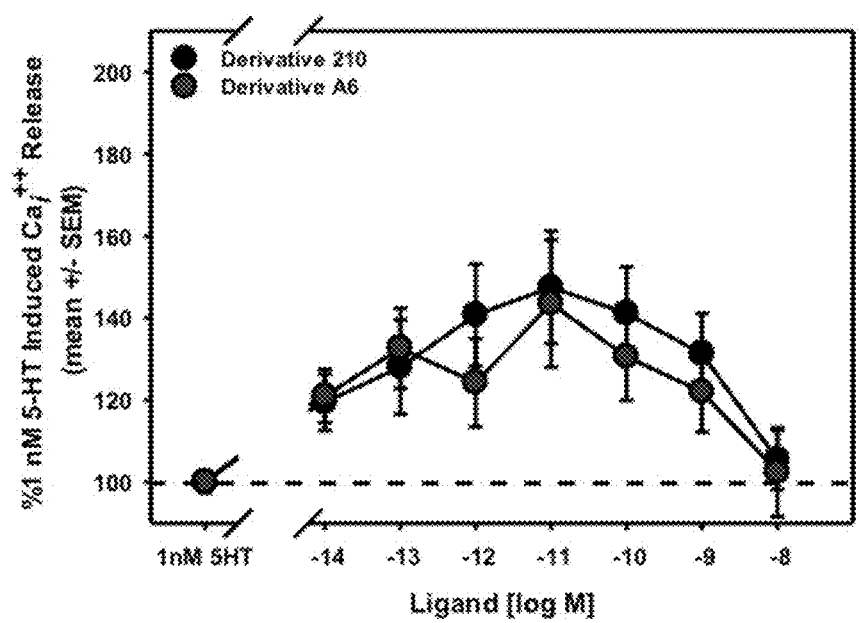
FIG. 20 compares the efficacy of derivatives 210 and A6 in terms of %1 nM 5-HT induced $Ca_i^{++}$ release in 5-HT$_{2C}$R-CHO cells.
Figure 21:
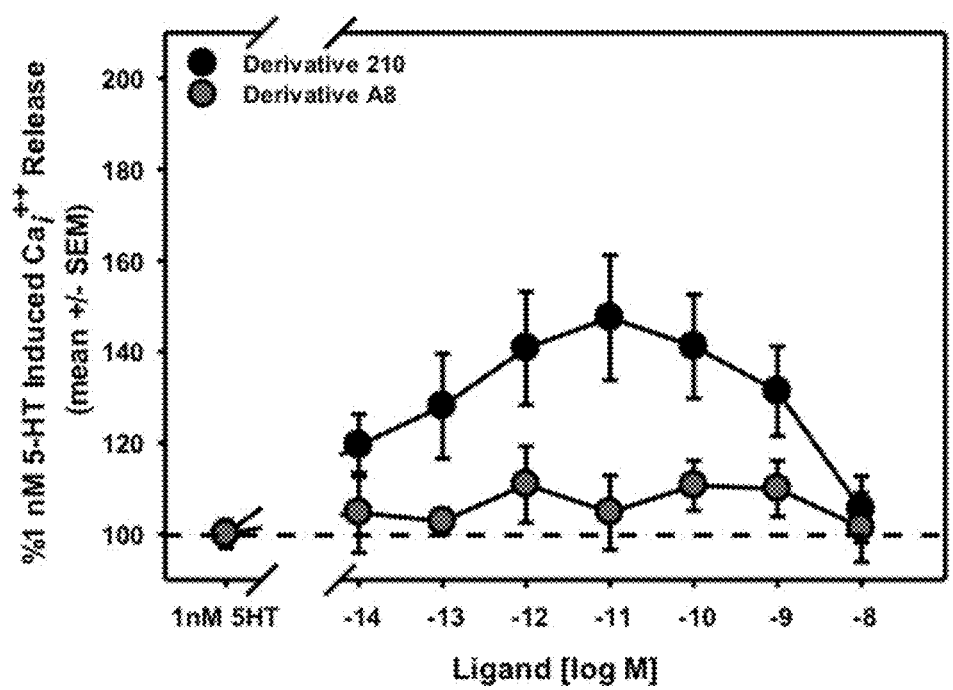
FIG. 21 compares the efficacy of derivatives 210 and A8 in terms of %1 nM 5-HT induced $Ca_i^{++}$ release in 5-HT$_{2C}$R-CHO cells.

Seven new peptides were generated based upon fragment 210 in which each individual molecule had a different residue replaced with an alanine (alanine scan). FIG. 15 compares the efficacy of derivatives 210 and A1 in terms of %1 nM 5-HT induced $\text{Ca}_i^{++}$ release in $5\text{-HT}_{2C}\text{R-CHO}$ cells. FIG. 16 compares the efficacy of derivatives 210 and A2 in terms of %1 nM 5-HT induced $\text{Ca}_i^{++}$ Release in $5\text{-HT}_{2C}\text{R-}$ CHO cells. FIG. 17 compares the efficacy of derivatives 210 and A3 in terms of %1 nM 5-HT induced $\text{Ca}_i^{++}$ release in $5\text{-HT}_{2C}\text{R-CHO}$ cells. FIG. 18 compares the efficacy of derivatives 210 and A4 in terms of %1 nM 5-HT induced $\text{Ca}_i^{++}$ release in $5\text{-HT}_{2C}\text{R-CHO}$ cells. FIG. 19 compares the efficacy of derivatives 210 and A5 in terms of %1 nM 5-HT induced $\text{Ca}_i^{++}$ release in $5\text{-HT}_{2C}\text{R-CHO}$ cells. FIG. 20 compares the efficacy of derivatives 210 and A6 in terms of %1 nM 5-HT induced $\text{Ca}_i^{++}$ release in $5\text{-HT}_{2C}\text{R-CHO}$ cells. FIG. 21 compares the efficacy of derivatives 210 and A8 in terms of %1 nM 5-HT induced $\text{Ca}_i^{++}$ release in $5\text{-HT}_{2C}\text{R-}$ CHO cells. Only the replacement of alanine at position A8 resulted in a complete loss of efficacy for fragment 210 suggesting that this portion of the peptide fragment is critical for the $5\text{-HT}_{2C}\text{R}$ interaction with PTEN.

Example 4

3L4F Alters Rat Behavior Upon Systemic Injection

Figure 22:
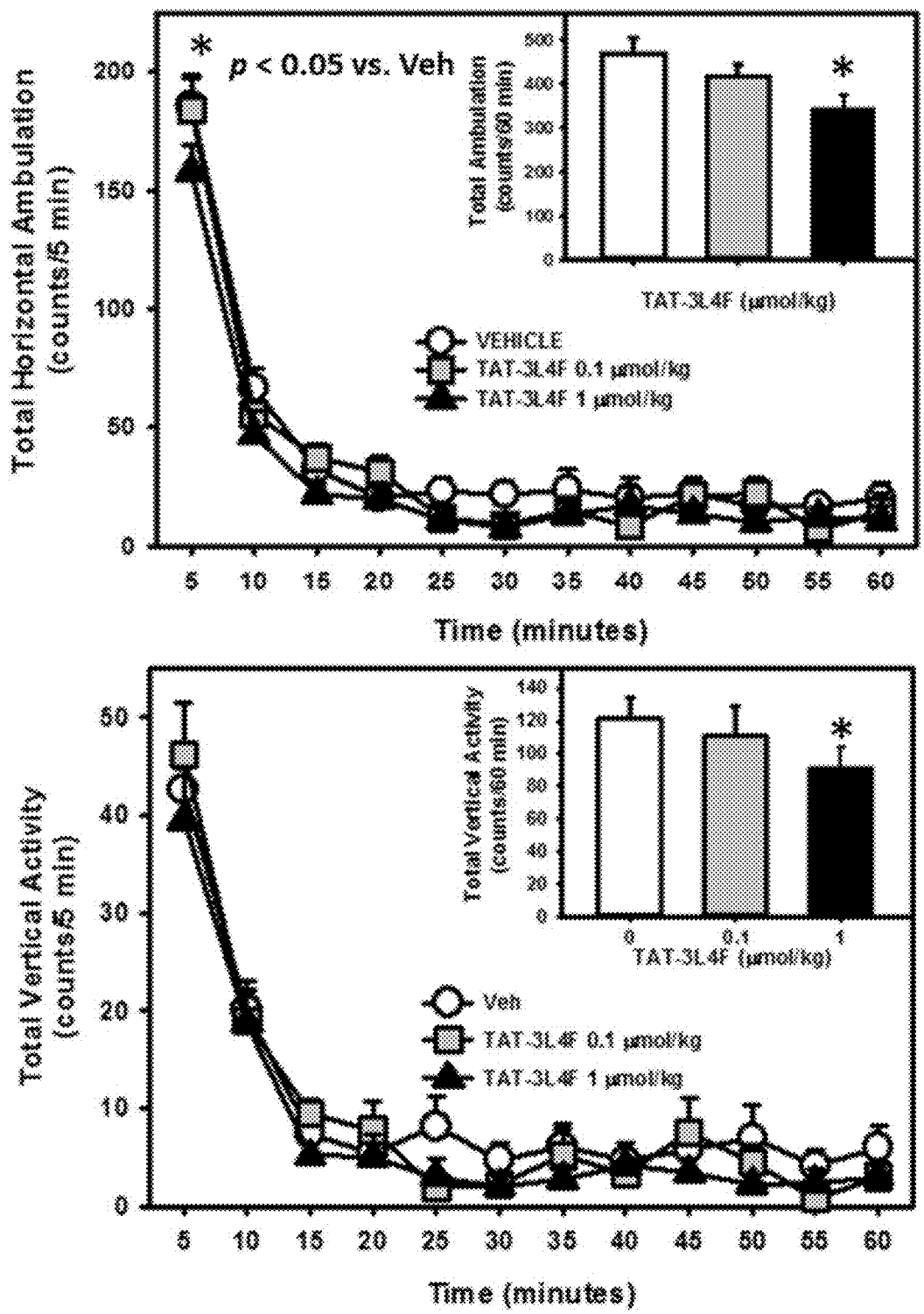
FIG. 22 shows a proof-of-concept study illustrating that TAT-3L4F administered intraperitoneally dose-dependently suppresses spontaneous locomotor activity in rats.
Figure 23:
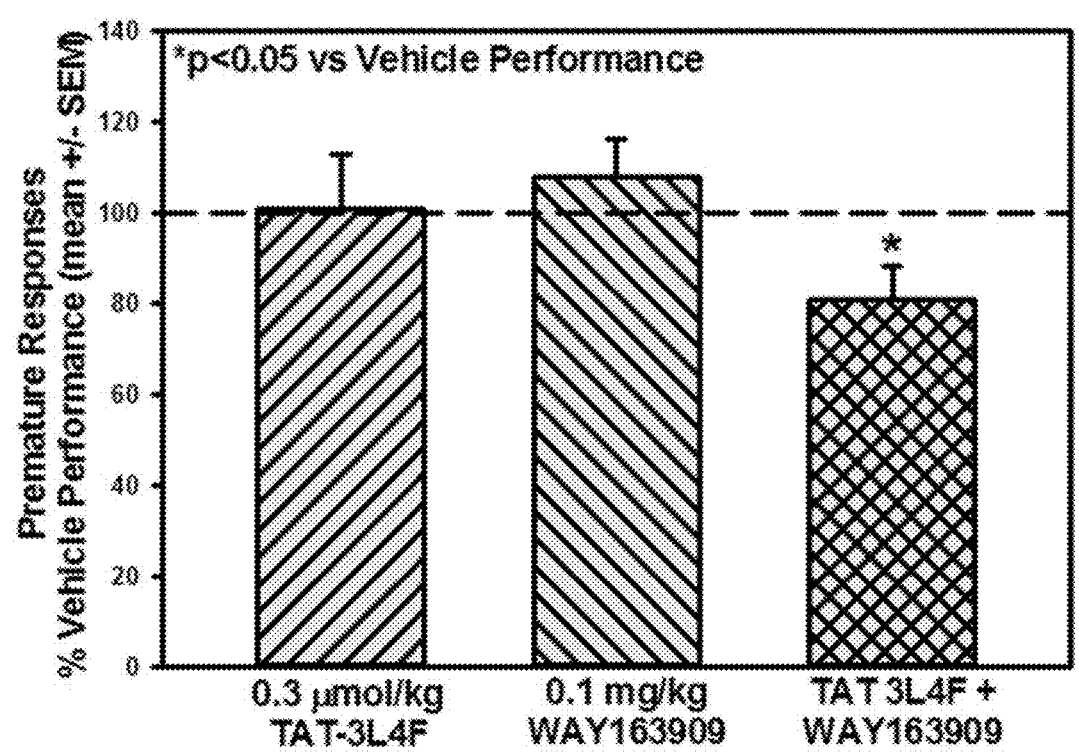
FIG. 23 illustrates additional behavioral effects of TAT-3L4F. An intraperitoneal dose of TAT-3L4F plus a dose of the selective 5-HT$_{2C}$R agonist WAY163909, neither of which have effects on their own, synergize to suppress impulsive action (premature responses) in rats trained on a 1-choice serial reaction time task.

FIG. 22 shows a proof-of-concept study illustrating that TAT-3L4F administered intraperitoneally dose-dependently suppresses spontaneous locomotor activity in rats. FIG. 23 illustrates additional behavioral effects of TAT-3L4F. An intraperitoneal dose of TAT-3L4F plus a dose of the selective $5\text{-HT}_{2C}\text{R}$ agonist WAY163909, neither of which have effects on their own, synergize to suppress impulsive action (premature responses) in rats trained on a 1-choice serial reaction time task. These data suggest that TAT-3L46 allosterically enhances $5\text{-HT}_{2C}\text{R}$ signaling generated by a submaximal dose of exogenous agonist.

The invention claimed is:

1. A method of activating 5-$HT_{2c}$ receptors (5-$HT_{2c}$R) signaling comprising administering to a human having an addiction to food, drugs, alcohol, or nicotine an effective amount of a peptide having an amino acid sequence of SEQ ID NO:2 or a functional variant thereof in combination with a 5-$HT_{2c}$R agonist, wherein the 5-$HT_{2c}$R agonist is WAY163909 and the functional variant is a peptide that has been modified by an amino terminal modification, a carboxy terminal modification, or an amino terminal modification and a carboxy terminal modification; or has a single amino acid substitution within the amino acid sequence of SEQ ID NO:2.

2. The method of claim 1, wherein the peptide has an amino acid sequence of SEQ ID NO:2.

* * * * *

SEQUENCE LISTING

<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Pro Asn Gln Asp Gln Asn Ala Arg Arg Arg Lys Lys Lys Glu Arg Arg
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Pro Asn Gln Asp Gln Asn Ala Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Asn Gln Asp Gln Asn Ala Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 4

Pro Xaa Gln Asp Gln Asn Ala Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Pro Asn Xaa Asp Gln Asn Ala Arg
1               5

```
<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Pro Asn Gln Xaa Gln Asn Ala Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Pro Asn Gln Asp Xaa Asn Ala Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 8

Pro Asn Gln Asp Gln Xaa Ala Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 9

Pro Asn Gln Asp Gln Asn Xaa Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Gln Asn Ala Arg Arg Arg Lys Lys
```

```
<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Arg Arg Lys Lys Lys Glu Arg Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Pro Asn Gln Asp Gln Asn Ala Ala
1               5
```